United States Patent
Brun et al.

(10) Patent No.: US 9,551,829 B2
(45) Date of Patent: *Jan. 24, 2017

(54) PHOTOACOUSTIC GAS SENSOR WITH A HELMHOLTZ CELL

(75) Inventors: Mickaël Brun, Eybens (FR); Sergio Nicoletti, Sinard (FR); Bertrand Parvitte, Reims (FR); Virginie Zeninari, Reims (FR)

(73) Assignees: Commissariat a l'energie atomique et aux energies alternatives (FR); Universite De Reims Champagne Ardenne (FR)

( * ) Notice: Subject to any disclaimer, the term of this patent is extended or adjusted under 35 U.S.C. 154(b) by 171 days.

This patent is subject to a terminal disclaimer.

(21) Appl. No.: 13/450,551

(22) Filed: Apr. 19, 2012

(65) Prior Publication Data
US 2012/0266655 A1    Oct. 25, 2012

(30) Foreign Application Priority Data
Apr. 21, 2011 (FR) ...................... 11 53471

(51) Int. Cl.
*G02B 6/028* (2006.01)
*G01N 21/17* (2006.01)
(Continued)

(52) U.S. Cl.
CPC ......... *G02B 6/0281* (2013.01); *G01N 21/1702* (2013.01); *G01N 29/2425* (2013.01);
(Continued)

(58) Field of Classification Search
CPC .... G01N 21/1702; G01N 21/17; G01N 21/63; G01N 2021/1704; G01N 2021/17; G01N 2021/1708; G01N 29/2425; G01N 29/2418; G01N 29/036; G01N 29/032; G01N 20/24; G01N 2201/0221; G01N 2291/021; G01N 2021/399; B82Y 15/00; B82Y 20/00; G02B 6/12; G02B 6/0281; G02B 6/132; G02B 6/12095; Y10T 29/49007
(Continued)

(56) References Cited

U.S. PATENT DOCUMENTS 5,157,461 A   10/1992   Page
5,783,839 A   7/1998   Morikawa et al.
(Continued)

FOREIGN PATENT DOCUMENTS

DE   102009029002 B3   1/2011
EP   2402735 A2   6/2011
(Continued)

OTHER PUBLICATIONS

Mario Mattiello et al., Novel Helholtz-based photoacoustic sensor for trace gas detection at ppm level using GaInAsSb/GaAlAsSb DFB lasers, Spectrochimica Acta Part A 63 (2006) 952-958.*
(Continued)

*Primary Examiner* — Hezrone E Williams
*Assistant Examiner* — Marrit Eyassu
(74) *Attorney, Agent, or Firm* — Kaplan Breyer Schwarz & Ottesen, LLP

(57) ABSTRACT

A photoacoustic detection device including a nanophotonic circuit including a first chip on which is formed at least one optical waveguide and in which is formed a set of cavities defining a Helmholtz resonator; at least one optical source capable of emitting an optical signal in a given wavelength range, capable of being modulated at an acoustic modulation frequency, this source being attached to the first chip; a second chip forming a cap for said cavities and including
(Continued)

acoustic sensors; and electronic circuits for processing the output of the acoustic sensors formed in the first or the second chip.

4 Claims, 3 Drawing Sheets

(51) Int. Cl.
*G01N 29/24* (2006.01)
*G01N 21/39* (2006.01)

(52) U.S. Cl.
CPC ........ *G01N 2021/1704* (2013.01); *G01N 2021/399* (2013.01); *G01N 2201/0221* (2013.01); *G01N 2291/021* (2013.01); *Y10T 29/49007* (2015.01)

(58) Field of Classification Search
USPC .................. 73/23.2, 24.01, 24.02, 24.06
See application file for complete search history.

(56) References Cited

U.S. PATENT DOCUMENTS

| | | | |
|---|---|---|---|
| 5,869,749 A * | 2/1999 | Bonne .................. | G01N 21/03 250/339.12 |
| 5,917,981 A | 6/1999 | Kovacic et al. | |
| 6,344,647 B1 * | 2/2002 | Jourdain et al. ........ | 250/339.07 |
| 6,618,148 B1 * | 9/2003 | Pilgrim et al. .............. | 356/432 |
| 6,677,655 B2 | 1/2004 | Fitzergald | |
| 6,765,211 B2 * | 7/2004 | Tapalian ................. | G01J 3/42 250/339.07 |
| 6,843,102 B1 | 1/2005 | Shulga et al. ............. | 73/25.01 |
| 7,304,732 B1 | 12/2007 | Polcawich et al. | |
| 7,398,672 B2 * | 7/2008 | Riddle ...................... | 73/24.06 |
| 8,768,132 B2 | 7/2014 | Stewart et al. | |
| 2002/0019101 A1 | 2/2002 | Kubo et al. | |
| 2002/0021879 A1 | 2/2002 | Lee et al. | |
| 2002/0174826 A1 | 11/2002 | Maydan et al. | |
| 2002/0194897 A1 * | 12/2002 | Arnott et al. ............... | 73/23.31 |
| 2004/0114853 A1 | 6/2004 | Bjorkman et al. | |
| 2005/0160791 A1 * | 7/2005 | Kung ........................ | 73/24.02 |
| 2006/0107744 A1 * | 5/2006 | Li ........................ | G01H 9/006 73/657 |
| 2006/0285114 A1 * | 12/2006 | Cao ...................... | B82Y 20/00 356/437 |
| 2006/0290944 A1 * | 12/2006 | Arnott et al. ............. | 356/519 |
| 2006/0292809 A1 | 12/2006 | Enicks et al. | |
| 2008/0144677 A1 | 6/2008 | Belkin et al. | |
| 2008/0277586 A1 * | 11/2008 | Cardinale ............... | 250/339.13 |
| 2009/0128819 A1 * | 5/2009 | Van Kesteren et al. ...... | 356/437 |
| 2009/0183552 A1 * | 7/2009 | Angster et al. ............ | 73/24.02 |
| 2010/0020326 A1 * | 1/2010 | Van Kesteren .............. | 356/437 |
| 2010/0177316 A1 | 7/2010 | So et al. | |
| 2011/0088453 A1 | 4/2011 | Nicoletti et al. | |
| 2012/0115310 A1 | 5/2012 | Miu et al. | |
| 2012/0151994 A1 * | 6/2012 | Hung et al. ................ | 73/24.02 |
| 2012/0328233 A1 * | 12/2012 | Chakravarty .......... | B82Y 20/00 385/12 |
| 2013/0315547 A1 | 11/2013 | Brun et al. | |

FOREIGN PATENT DOCUMENTS

| | | |
|---|---|---|
| EP | 2515096 A1 | 10/2012 |
| FR | 2815122 A1 | 4/2002 |
| FR | 2951545 A1 | 4/2011 |
| WO | 03083455 A1 | 10/2003 |
| WO | 2008074442 A1 | 6/2008 |

OTHER PUBLICATIONS

French Search Report dated Dec. 9, 2011 for French Patent Application No. 1153471 (FA752272).
"Non-Final Office Action" dated Dec. 31, 2014, issued in counterpart divisional U.S. Appl. No. 13/952,472 (now abandoned).
B. Ben Bakir et al., "Electrically driven hybrid Si/III-V Fabry-Perot lasers based on adiabatic mode transformers", "Optics Express", May 11, 2011, vol. 19, No. 11, Publisher: Optical Society of America, Published in: US.
"French Search Report" issued in French Patent Application No. 1453101, dated Jan. 14, 2015, which is a foreign counterpart of related U.S. Appl. No. 14/677,222.
Samara Louise Firebaugh, "Miniaturization and Integration of Photoacoustic Detection", May 25, 2001, Publisher: Massachusetts Institute of Technology, Published in: US.

* cited by examiner

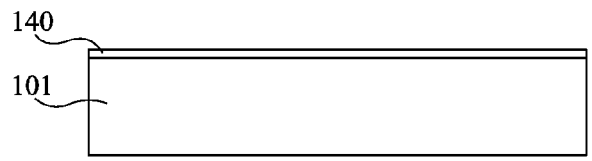
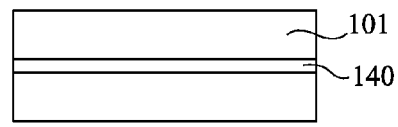
Fig 3A　　　Fig 4A
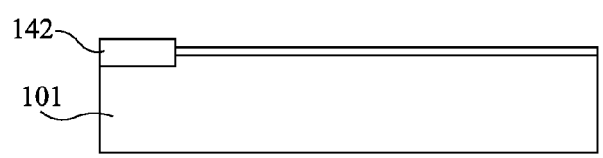
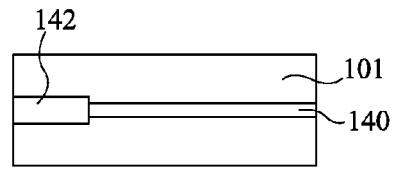
Fig 3B　　　Fig 4B
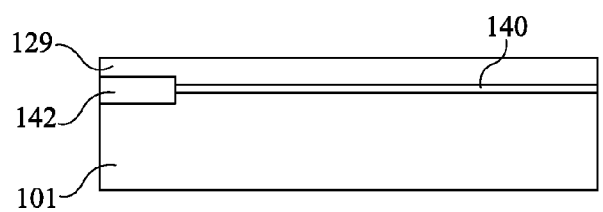
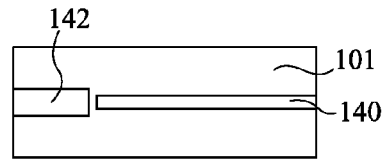
Fig 3C　　　Fig 4C
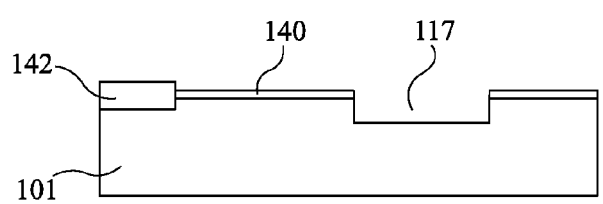
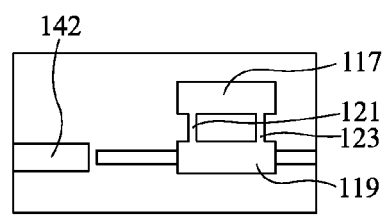
Fig 3D　　　Fig 4D

PHOTOACOUSTIC GAS SENSOR WITH A HELMHOLTZ CELL

BACKGROUND

Technical Field

The present disclosure relates to a photoacoustic-type gas detection device and more specifically to a sensor based on a Helmholtz resonator.

Discussion of the Art

A photoacoustic gas detection device with discrete components using a sensor based on a Helmholtz resonator is described in FR2815122, FIG. 1 of this application being reproduced as FIG. 1 of the drawings.

This device comprises a light source (laser) 1 modulated by a mechanical modulator 2 at an acoustic frequency. Modulated beam 3 is sent into a tube 40 of a resonant Helmholtz cell 4 containing a gas mixture to be analyzed. This cell comprises a second tube 41 parallel to the first one. The two tubes are connected by capillaries 43 and 44. By properly selecting the length and the diameter of the tubes and of the capillaries, a cell at a selected resonance frequency can be formed. The acoustic resonance frequency is adapted to the modulation frequency imposed by modulator 2 (or conversely). An electret microphone 10, 11 is associated with each of tubes 40, 41. The microphone outputs are sent to a differential amplifier 8. The output of this amplifier provides a display system 9 with electric signals representative of the amount of gas present. The device also comprises an electronic assembly 7 enabling to control the mechanical modulator. Thus, when the laser wavelength corresponds to an absorption stripe of a gas, the presence of this gas and its concentration can be determined.

However, such a gas detection device formed based on discrete elements remains limited to laboratory applications. Indeed:

- it is difficult to find materials usable with discrete elements with transmission wavelengths greater than 2.5 μm while it would be desirable for a gas analysis to be possible at wavelengths in more remote infrared, within a range from 3 to 10 μm;
- the device is generally sensitive to temperature variations and to vibrations which may disturb the alignment;
- the implementation of the system, that is, the positioning of its elements and their alignment, must be performed by means of very accurate optical benches, which are very difficult to handle;
- the macroscopic size of the device prevents "sensor"-type applications capable of competing with non-selective chemical sensors;
- it is not possible, with such a device, to scan a wide range of wavelengths and it is very difficult to replace the laser source.

Photoacoustic gas detection devices overcoming the disadvantages of known devices are thus needed.

BRIEF SUMMARY

Thus, an object of an embodiment of the present invention is to provide a photoacoustic detection device having at least some of the following features:

stability,
insensitivity to vibrations,
great accuracy,
very small dimensions,
ability to operate at several wavelengths for example ranging between 3 and 10 μm,
ability to be easily transported, enabling to work during the transportation.

An embodiment of the present invention provides a photoacoustic detection device comprising a nanophotonic circuit comprising a first chip on which is formed at least one optical waveguide and in which is formed a set of cavities defining a Helmholtz resonator; at least one optical source capable of emitting an optical signal in a given wavelength range, capable of being modulated at an acoustic modulation frequency, this source being attached to the first chip; a second chip forming a cap for said cavities and comprising acoustic sensors; and electronic circuits for processing the output of the acoustic sensors formed in the first or the second chip.

According to an embodiment of the present invention, the device comprises on the first chip a set of waveguides, each waveguide being associated with a laser linked to the first chip.

According to an embodiment of the present invention, said at least one optical source is formed in a third chip placed on a recessed portion of the first chip.

According to an embodiment of the present invention, said at least one optical source comprises at least one QCL-type laser.

According to an embodiment of the present invention, the end of the waveguide(s) on the side of said at least one optical source is arranged as an optical coupler.

An embodiment of the present invention provides a method for manufacturing a photoacoustic detection device such as hereabove, comprising the steps of:

forming on a first chip at least one optical waveguide;
placing on the first chip at least one laser source;
depositing an encapsulation layer;
hollowing the encapsulation layer, the underlying layers, and the substrate to define the cavities of a Helmholtz resonator;
coating the region where the cavities are formed with a second chip forming a cap and comprising acoustic sensors;
forming in one of the first and second chips electronic processing circuits.

The foregoing and other features and advantages of the present invention will be discussed in detail in the following non-limiting description of specific embodiments in connection with the accompanying drawings.

BRIEF DESCRIPTION OF THE DRAWINGS

FIGS. 3A to 3D and 4A to 4D are respective cross-section views and top views of the detection device of FIGS. 2A and 2B at intermediate steps of an example of a method for manufacturing this device.

As usual in the representation of microcomponents, the various dimensions, and especially the layer thicknesses, are not to scale. Those skilled in the art will refer to current literature on the topic and/or to the specific indications given hereafter as an example.

DETAILED DESCRIPTION

An embodiment of the present invention provides forming a monolithic photoacoustic detection device. All microoptical, microelectronic, and acoustic components are formed on a same support by using micro- and nano-manufacturing techniques typical of microelectronics and of microelectromechanical systems (MEMS). This ensures a degree of dimensional control, a structural stiffness, and a robustness which go far beyond what can be obtained with an assembly of discrete elements. This integration of the different components on a same substrate makes it possible to accurately control the temperature of the entire detection device by, for example, using a Peltier-effect cooler. This is particularly important due to the fact that laser sources operating in middle infrared, such as so-called quantum cascade lasers, are generally sensitive to temperature variations, which may cause wavelength shifts. Further, forming on a same support an integrated amplifier close to the optical, acoustic, and electronic elements enables to decrease the noise by amplifying low signals in an amplifier integrated in the same device. A considerable gain in signal-to-noise ratio is thus obtained. Finally, the device, due to its miniaturization and to its portability, is usable in circumstances where a device with discrete elements could not be used.

More specifically, the detection device may comprise several integrated laser sources, which may be selectively activated and directed towards a same waveguide transmitting their beam towards an integrated Helmholtz cell. This solves the alignment problems of prior art devices.

Figure 1:
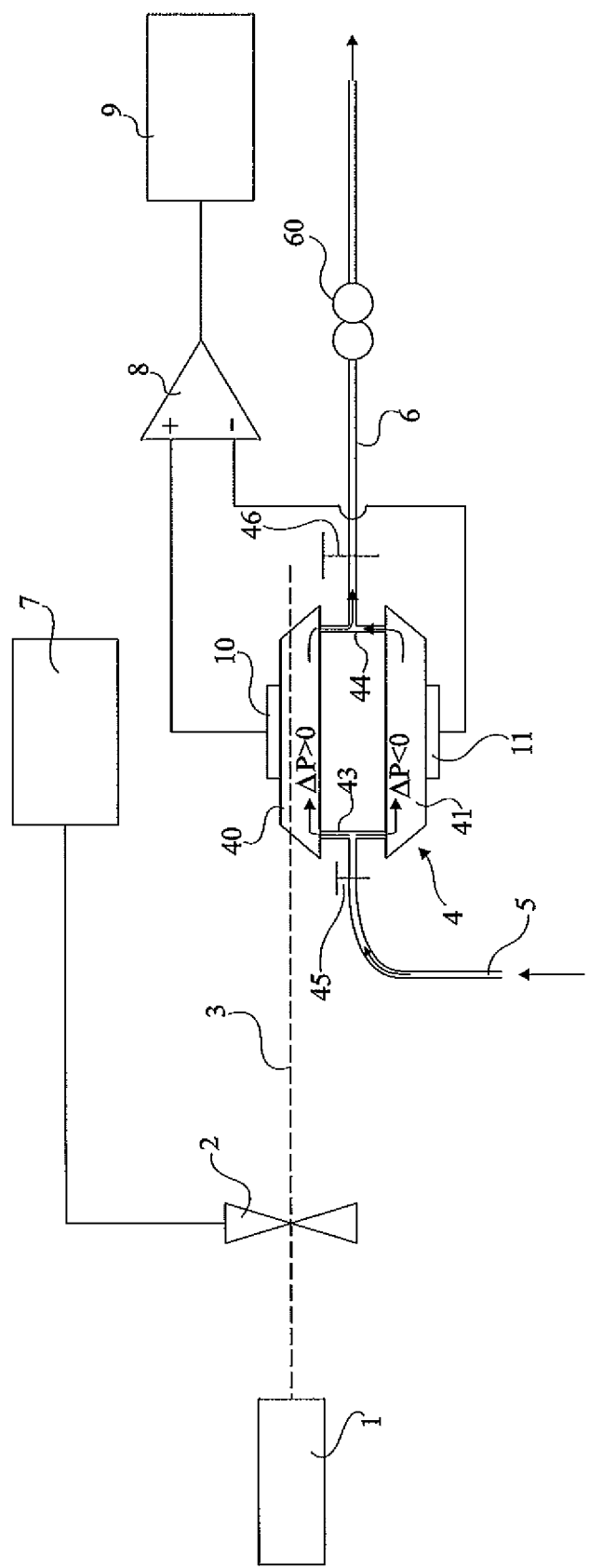
FIG. 1, previously described, shows FIG. 1 of FR2815122.
Figure 2A:
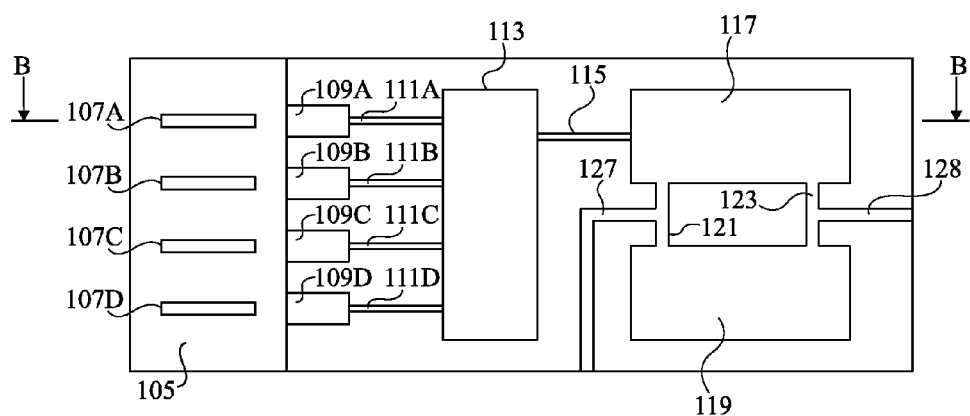
FIG. 2A is a simplified top view of a detection device according to an embodiment of the present invention.
Figure 2B:
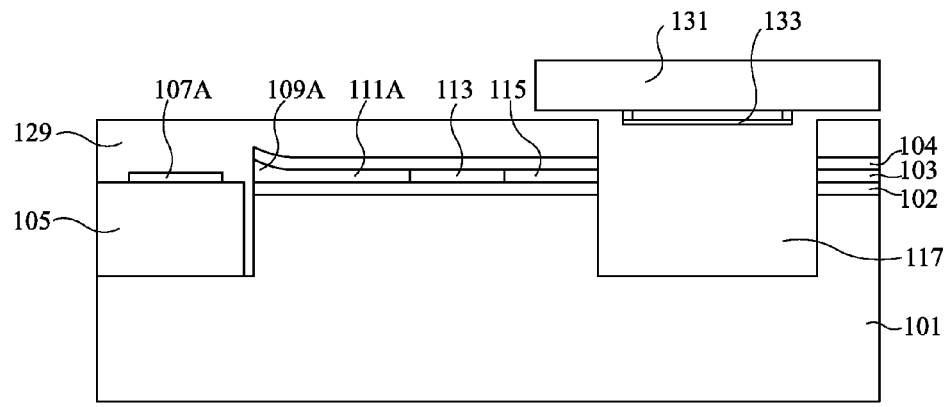
FIG. 2B is a cross-section view along plane BB of FIG. 2A.

FIGS. 2A to 2B respectively are a top view and a cross-section view along plane BB of FIG. 2A, illustrating an embodiment of a microsensor according to the present invention.

These drawings are extremely simplified and are only intended to ease the understanding of an embodiment of the present invention.

FIGS. 2A and 2B, where the same reference numerals designate the same elements, will be generically described.

The entire structure is formed on a single substrate 101, generally a silicon wafer coated with three layers 102, 103, 104, examples of which will be given hereinafter. Waveguides are defined in layer 103, layers 102 and 104 forming cladding layers. Assembly 102, 103, 104 may be either a trilayer (Si/Ge/Si or SiN/Si/SiN), or an epitaxial SiGe-on-Si layer having its Ge proportion varying to create an index gradient of triangular or trapezoidal profile covered with an Si cladding layer (epitaxial or amorphous).

On a hollowed portion of support 101 is placed an element 105 on which semiconductor lasers, preferably of QCL (Quantum Cascade Laser) type, are formed. As an example, this assembly may be performed according to so-called heterogeneous hybridization techniques currently used in micro- and nano-manufacturing technologies. 4 lasers 107A to 107D, which are normally set to different frequencies preferably ranging between 3 and 10 μm, have been shown. In practice, a larger number of lasers may be used, for example, 6 lasers respectively operating at wavelengths of 4.0, 4.2, 4.4, 4.6, 4.8, 5.0 μm to cover the range from 4 to 5 μm. An advantage of QCL lasers is their miniaturization capacity and their capacity of setting the transmission wavelength, that is, each of these lasers may have a wavelength slightly variable around its reference wavelength, where this wavelength adjustment may for example result from the selection of bias currents.

According to an alternative embodiment of the present invention, the layers of materials necessary to the forming of QCL lasers are directly transferred onto the support, for example, by a molecular bonding method. QCL lasers will then be directly formed on the final support. In a second version, the entire laser may be transferred by low-temperature polymer-type bonding.

Lasers are associated with means, not shown, of power supply and modulation at an acoustic frequency. These lasers emit their radiation towards respective couplers 109A to 109D, for example, of three-dimensional taper coupler type. Such couplers couple laser beams towards respective optical waveguides 111A to 111D connected to the inputs of an optical multiplexer 113. The multiplexer sends back the incident light of a selected one of input waveguides 111A to 111D to an output waveguide 115. Waveguide 115 emerges in a first shell 117 of a Helmholtz resonator. This Helmholtz comprises a second shell 119 identical to the first one and connected thereto by capillaries 121 and 123. A gas input 127 is formed in the middle of capillary 121 and a gas output 128 is formed in the middle of capillary 123. Tubes 117, 119 and capillaries 121, and 123 correspond to recesses formed in substrate 101 and all the layers which cover it. It should be noted that, above the entire structure, before forming the recesses, a layer 129, for example, $SiO_2$, having a thickness ranging from 1 to 10 μm, will have preferably been formed over the entire structure. Thus, the top of cavities 117, 119 and 121, 123, which have respective depths approximately ranging from 10 to 50 and from 1 to 5 μm, is clearly above the level at which waveguide 115 emerges in cavity 117.

The cavities are closed by a cap 131, preferably a silicon chip, which comprises acoustic sensors 133 and means of connection to these sensors (not shown).

Chip 131 or chip 101 also comprises integrated electronic circuits capable of processing the sensor signals.

According to an advantage of the present invention, all the components described hereabove may be simply formed based on a small number of layers of a nanophotonic integrated circuit.

More specifically, waveguides 111 and 115 are formed from a same assembly of layers that may be such as described hereabove or that may be different, according to the available manufacturing technologies and according to the targeted wavelength range.

According to an embodiment adapted to an operation in a wavelength range between 3 and 10 μm where the light-gas interaction is maximum, layer 102 is a silicon layer, the couplers and the cores of the optical waveguides are formed in a germanium layer 103 and cladding layer 104 also is a silicon layer. Given that the germanium layer and the silicon cladding layer are obtained by growth above a single-crystal semiconductor layer, they may favorably be single-crystal layers. These layers may also be replaced with a SiGe layer comprising a variable Ge concentration along the direction perpendicular to the substrate, thus forming a layer with a gradient index which may have a triangular or trapezoidal profile.

According to another alternative embodiment, the support layer of each waveguide may be made of silicon and the cladding layer may also be made of silicon nitride. This embodiment is particularly well adapted to an operation within a wavelength range from 3 to 6 μm.

The operating mode of the Helmholtz cell sensor will not be described in detail since, as to principles, it is identical to that of a discrete system, with the advantage of being able to operate simultaneously with several integrated lasers, and to be able to operate within a wide range of wavelengths, given the specific features of integrated waveguides.

It should be understood that, if an SOI-type structure is used, the various electronic components intended for the amplification of the signals and for their analysis may be formed in the same structure.

Various embodiments with different variations have been described hereabove. Those skilled in the art may combine various elements of these various embodiments and variations without showing any inventive step.

As a variation, instead of being coupled to waveguide(s) 111 by couplers 109, laser(s) 107 could be arranged above these waveguides 109 and be coupled by evanescent waves.

FIGS. 3A to 3D and 4A to 4D respectively are cross-section views and top views illustrating successive steps of an example of a method for manufacturing a detection device according to an embodiment of the present invention.

FIGS. 3A and 4A show a substrate 101 coated with an assembly of layers 102, 103, 104 shown in the form of a single layer 140. This structure may correspond to a silicon-on-insulator (SOI) wafer where the above-mentioned layers generally are a silicon oxide layer and a silicon layer. It could however be started from any substrate compatible with a micro- and nano-manufacturing technology. The first layer may result from the deposition and/or from an epitaxial growth of a layer having a first optical index $n_{cl}$, typically silicon, but also for example $MgF_2$, $CaF_2$, $SrF_2$, $BaF_2$, $PbF_2$, CdF, GaAs, AlGaAs, InP, InAs, InSb, ZnS, CdTe, or $Al_2O_3$. The second layer may result from any deposition and/or from an epitaxial growth of a layer having an optical index $n_c > n_{cl}$, typically SiGe or Ge, but also possibly $MgF_2$, $CaF_2$, $SrF_2$, $BaF_2$, $PbF_2$, CdF, GaAs, AlGaAs, InP, InAs, InSb, ZnS, CdTe, or $Al_2O_3$. It should be noted that the second layer is especially intended to form the core of an optical waveguide and $n_c$ designates the index of this core. The first layer is especially intended to form the optical cladding layer of an optical waveguide, whereby its index is named $n_{cl}$.

The second layer is etched to form photonic components (guide, coupler, multiplexer, focusing or filtering device if necessary). Advantageously, these patterns are manufactured by structuring of a simple layer by photolithography and selective etching. The portion corresponding to the waveguides is coated with a second optical cladding layer of index $n_{cl2} < n_c$. This cladding layer will typically be made of silicon and may be made of $MgF_2$, $CaF_2$, $SrF_2$, $BaF_2$, $PbF_2$, CdF, GaAs, AlGaAs, InP, InAs, InSb, ZnS, CdTe, or $Al_2O_3$ to define the guide structure. Advantageously, the material of the second cladding layer will be the same as that selected for the first cladding layer.

At the step illustrated in FIGS. 3B and 4B, substrate 101 is etched to receive a chip 142 containing the different laser source(s). Chip 142 is transferred, aligned, and attached to substrate 101 by a ball surface mounting or by eutectic bonding, for example, a gold layer on the substrate and a Sn layer on the chip and a thermal processing to form an Au—Sn alloy. According to a variation, the laser(s) may be formed by transfer of the multilayer forming the active medium of a QCL laser by molecular bonding, and the substrate having received the multilayer growth (typically GaAs) is bonded to the main substrate on the multilayer side. The GaAs is then removed. After this, the layer is shaped as described, for example, in Applied Physics Letters 91 (2007) 231101 to form the active QCL laser.

At the step illustrated in FIGS. 3C and 4C, the entire structure is coated with an encapsulation layer corresponding to layer 129 mentioned in relation with FIG. 2B.

At the step illustrated in FIGS. 3D and 4D, encapsulation layer 129, underlying layers 140 and substrate 101 are hollowed at the locations where cavities 117, 119, 121, and 123 are desired to be formed. Then, the structure of cap 131 described in relation with FIG. 2B is coated to obtain the final integrated component.

Such alterations, modifications, and improvements are intended to be part of this disclosure, and are intended to be within the spirit and the scope of the present invention. Accordingly, the foregoing description is by way of example only and is not intended to be limiting. The present invention is limited only as defined in the following claims and the equivalents thereto.

What is claimed is:

1. A photoacoustic detection device comprising a nanophotonic circuit comprising:
    a first chip on which is formed at least one optical waveguide and in which is formed a set of cavities defining a Helmholtz resonator, each of the cavities having an opening;
    at least one optical source configured to emit an optical signal in a given wavelength range, and configured to be modulated at an acoustic modulation frequency, this source being attached to the first chip;
    a second chip forming a cap, which closes the openings of said cavities and comprising acoustic sensors;
    electronic circuits for processing the output of the acoustic sensors formed in the first or the second chip; and
    a set of waveguides on the first chip, each waveguide being associated with an optical source linked to the first chip.

2. The device of claim 1, wherein said at least one optical source is formed in a third chip placed on a recessed portion of the first chip.

3. The device of claim 1, wherein said at least one optical source comprises at least one QCL-type laser.

4. The device of claim 1, wherein the end of the at least one waveguide on the side of said at least one optical source is arranged as an optical coupler.

* * * * *